US010899692B2

(12) United States Patent
Nishizawa et al.

(10) Patent No.: US 10,899,692 B2
(45) Date of Patent: Jan. 26, 2021

(54) PURIFICATION METHOD AND PRODUCTION METHOD OF DIFLUOROMETHYL-1, 2, 2, 2-TETRAFLUOROETHYL ETHER

(71) Applicant: Central Glass Company, Limited, Ube (JP)

(72) Inventors: Eri Nishizawa, Kawagoe (JP); Shinya Akiba, Kawagoe (JP)

(73) Assignee: Central Glass Company, Limited, Ube (JP)

( * ) Notice: Subject to any disclaimer, the term of this patent is extended or adjusted under 35 U.S.C. 154(b) by 0 days.

(21) Appl. No.: 16/955,598

(22) PCT Filed: Oct. 26, 2018

(86) PCT No.: PCT/JP2018/039795
§ 371 (c)(1),
(2) Date: Jun. 18, 2020

(87) PCT Pub. No.: WO2019/123834
PCT Pub. Date: Jun. 27, 2019

(65) Prior Publication Data
US 2020/0339494 A1    Oct. 29, 2020

(30) Foreign Application Priority Data

Dec. 22, 2017  (JP) ................... 2017-246631

(51) Int. Cl.
C07C 41/38 (2006.01)
C07C 41/44 (2006.01)
C07C 43/12 (2006.01)
C07C 41/22 (2006.01)
C07C 45/63 (2006.01)
C07C 41/01 (2006.01)
B01J 27/24 (2006.01)

(52) U.S. Cl.
CPC ............ *C07C 41/38* (2013.01); *C07C 41/01* (2013.01); *C07C 41/22* (2013.01); *C07C 41/44* (2013.01); *C07C 43/123* (2013.01); *C07C 45/63* (2013.01); *B01J 27/24* (2013.01)

(58) Field of Classification Search
CPC ....... C07C 41/38; C07C 43/123; C07C 41/44; C07C 41/22; C07C 41/01; C07C 45/63; B01J 27/24
See application file for complete search history.

(56) References Cited

U.S. PATENT DOCUMENTS

| 4,972,040 | A | 11/1990 | Robin et al. |
| 5,205,914 | A | 4/1993 | Rozov et al. |
| 5,458,674 | A | 10/1995 | Barsotti |
| 6,054,626 | A | 4/2000 | Chambers et al. |
| 7,230,142 | B1 | 6/2007 | Kawai et al. |
| 2008/0306309 | A1 | 12/2008 | Mazzell et al. |
| 2011/0082313 | A1 | 4/2011 | Ishii et al. |
| 2019/0345086 | A1* | 11/2019 | Hosoi ............. C07C 41/01 |

FOREIGN PATENT DOCUMENTS

| DE | 23 61 058 A | 6/1975 |
| EP | 0 151 697 A1 | 8/1985 |
| GB | 2 219 292 A | 6/1989 |
| JP | 60-112724 A | 6/1985 |
| JP | 1-301636 A | 12/1989 |
| JP | 2-104545 A | 4/1990 |
| JP | 4-273839 A | 9/1992 |
| JP | 6-87777 A | 3/1994 |
| JP | 9-501694 A | 2/1997 |
| JP | 10-101595 A | 4/1998 |
| JP | 11-180923 A | 7/1999 |
| JP | 11-246459 A | 9/1999 |
| JP | 2008-530118 A | 8/2008 |
| JP | 2009-286731 A | 12/2009 |

OTHER PUBLICATIONS

International Search Report (PCT/ISA/210) issued in PCT Application No. PCT/JP2018/039795 dated Dec. 4, 2018 with English translation (four (4) pages).
Japanese language Written Opinion (PCT/ISA/237) issued in PCT Application No. PCT/JP2018/039795 dated Dec. 4, 2018 (three (3) pages).

* cited by examiner

*Primary Examiner* — Jafar F Parsa
(74) *Attorney, Agent, or Firm* — Crowell & Moring LLP

(57) ABSTRACT

A purification method of desflurane (difluoromethyl-1,2,2,2-tetrafluoroethyl ether of the formula (1)) includes bringing a mixture containing desflurane and a trihalomethane into contact with a base in the presence of a phase transfer catalyst, thereby decomposing the trihalomethane. By this method, only the trihalometane contained as a by-product in the desflurane is decomposed without causing decomposition of the desflurane, whereby the desflurane is obtained with high purity.

(1)

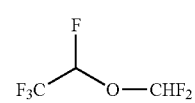

8 Claims, No Drawings

PURIFICATION METHOD AND PRODUCTION METHOD OF DIFLUOROMETHYL-1, 2, 2, 2-TETRAFLUOROETHYL ETHER

FIELD OF THE INVENTION

The present invention relates to a purification method and production method of difluoromethyl-1,2,2,2-tetrafluoroethyl ether, which is known as an inhalation anesthetic.

BACKGROUND ART

It is known that difluoromethyl-1,2,2,2-tetrafluoroethyl ether (generic name: desflurane; hereinafter also referred to as "desflurane") is a general inhalation anesthetic capable of obtaining an adequate depth of anesthesia and allowing a good awakening.

One known production method of desflurane is to form dichloromethyl-1,2,2,2-tetrafluoroethyl ether of the formula (3) by chlorination of methyl-1,2,2,2-tetrafluoroethyl ether of the formula (2) with chlorine, and then, form desflurane of the formula (1) by fluorination of the dichloromethyl-1, 2,2,2-tetrafluoroethyl ether with anhydrous hydrogen fluoride, as disclosed in Patent Documents 1 to 3.

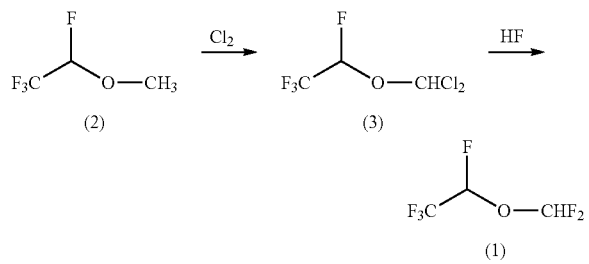

PRIOR ART DOCUMENTS

Patent Documents

Patent Document 1: German Patent No. 2361058
Patent Document 2: Japanese Laid-Open Patent Publication No. H2-104545
Patent Document 3: Japanese Laid-Open Patent Publication No. H6-087777

SUMMARY OF THE INVENTION

Problems to be Solved by the Invention

It is an object of the present invention to provide a purification method and production method for obtaining desflurane with high purity.

Means for Solving the Problems

The present inventors carried out fluorination of dichloromethyl-1,2,2,2-tetrafluoroethyl ether of the formula (3) with anhydrous hydrogen fluoride to synthesize desflurane of the formula (1). Consequently, there were formed not only desflurane but also chlorofluoromethyl-1,2,2,2-tetrafluoroethyl ether of the formula (4), chloroform of the formula (A) and dichlorofluoromethane of the formula (B) as by-products (see the after-mentioned Example: [Preparation Example 1]).

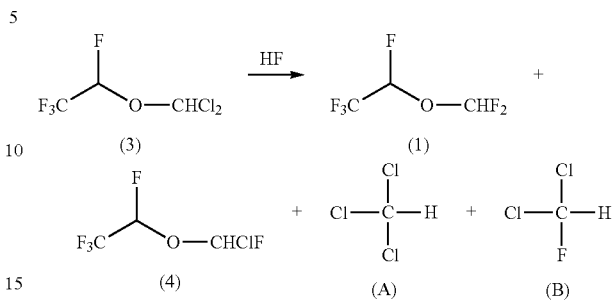

Herein, the chlorofluoromethyl-1,2,2,2-tetrafluoroethyl ether of the formula (4) is a compound obtained by replacing one chlorine atom of dichloromethyl-1,2,2,2-tetrafluoroethyl ether of the formula (3) with a fluorine atom, and is converted to the desflurane by replacing another chlorine atom of the chlorofluoromethyl-1,2,2,2-tetrafluoroethyl ether with a fluorine atom. It is assumed that, as a result of the fluorination being carried out under harsh condition using the anhydrous hydrogen fluoride, chloroform and dichlorofluoromethane were formed by cleavage of ether moieties (—O—) of the ethers of the formulas (1), (3) and (4).

The present inventors subsequently performed precision distillation of the reaction product containing the desflurane, chlorofluoromethyl-1,2,2,2-tetrafluoroethyl ether, chloroform and dichlorofluoromethane for the purpose of removing the by-products such as chlorofluoromethyl-1,2,2,2-tetrafluoroethyl ether, chloroform and dichlorofluoromethane and obtaining only the desflurane. Then, the chloroform was not removed although the chlorofluoromethyl-1,2,2,2-tetrafluoroethyl ether and dichlorofluoromethane were removed.

The present inventors have found that the reason that the chloroform cannot be removed is that the chloroform forms an azeotrope with the desflurane and thus cannot be separated from the desflurane (see the after-mentioned Example: [Confirmation of Azeotrope between Desflurane and Chloroform]).

The present inventors have made extensive researches to solve this problem and resultantly found that, when desflurane containing chloroform is brought into contact with a base in the presence of water and a phase transfer catalyst, there occurs decomposition of the chloroform, but surprisingly does not occur decomposition of the desflurane. The present inventors have also found that the other trihalomethanes are decomposed in the same manner as the chloroform. The present invention has been accomplished based on these findings.

Accordingly, the present invention includes the following inventive aspects 1-9.

[Inventive Aspect 1]

A purification method of difluoromethyl-1,2,2,2-tetrafluoroethyl ether, comprising bringing a mixture containing difluoromethyl-1,2,2,2-tetrafluoroethyl ether of the formula (1) and a trihalomethane into contact with a base in the presence of water and a phase transfer catalyst, thereby decomposing the trihalomethane.

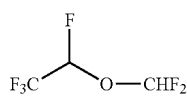
(1)

[Inventive Aspect 2]
The purification method of difluoromethyl-1,2,2,2-tetrafluoroethyl ether according to Inventive Aspect 1, wherein the trihalomethane is chloroform.

[Inventive Aspect 3]
The purification method of difluoromethyl-1,2,2,2-tetrafluoroethyl ether according to Inventive Aspect 1 or 2, wherein the phase transfer catalyst is an ammonium salt phase transfer catalyst.

[Inventive Aspect 4]
The purification method of difluoromethyl-1,2,2,2-tetrafluoroethyl ether according to any one of Inventive Aspects 1 to 3, wherein the phase transfer catalyst is used in an amount of 0.001 mass % to 30 mass % based on the total mass of the difluoromethyl-1,2,2,2-tetrafluoroethyl ether.

[Inventive Aspect 5]
The purification method of difluoromethyl-1,2,2,2-tetrafluoroethyl ether according to any one of Inventive Aspects 1 to 4, wherein the base is an alkali metal hydroxide.

[Inventive Aspect 6]
The purification method of difluoromethyl-1,2,2,2-tetrafluoroethyl ether according to Inventive Aspect 5, wherein the alkali metal hydroxide is used in an amount of 0.001 mass % to 100 mass % based on the total mass of the difluoromethyl-1,2,2,2-tetrafluoroethyl ether.

[Inventive Aspect 7]
The purification method of difluoromethyl-1,2,2,2-tetrafluoroethyl ether according to any one of Inventive Aspects 1 to 6, wherein the mixture is brought into contact with the base in the presence of the phase transfer catalyst at a temperature of 5° C. to 50° C.

[Inventive Aspect 8]
A production method of difluoromethyl-1,2,2,2-tetrafluoroethyl ether, comprising purifying difluoromethyl-1,2,2,2-tetrafluoroethyl ether by the purification method according to any one of Inventive Aspects 1 to 7.

[Inventive Aspect 9]
The production method of difluoromethyl-1,2,2,2-tetrafluoroethyl ether according to Inventive Aspect 8, further comprising:
forming dichloromethyl-1,2,2,2-tetrafluoroethyl ether of the formula (3) by chlorination of methyl-1,2,2,2-tetrafluoroethyl ether of the formula (2) with chlorine; and
forming difluoromethyl-1,2,2,2-tetrafluoroethyl ether of the formula (1) by fluorination of the dichloromethyl-1,2,2,2-tetrafluoroethyl ether with anhydrous hydrogen fluoride.

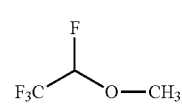
(2)

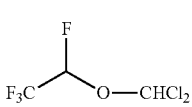
(3)

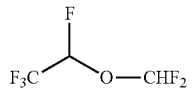
(1)

Effects of the Invention

By the purification method of desflurane according to the present invention, only the trihalometane contained as a by-product in the desflurane is decomposed without causing decomposition of the desflurane, whereby the desflurane is obtained with high purity.

DETAILED DESCRIPTION OF THE EMBODIMENTS

Hereinafter, the present invention will be described in detail below. It should be understood that: the following embodiments are not intended to limit the present invention thereto; various changes and modifications can be made to the following embodiments, based on the common knowledge of those skilled in the art, within the range that does not impair the effects of the present invention; and such changes and modifications are also included in the scope of the present invention.

As a method for decomposition of chloroform, there is known Reimer-Tiemann Reaction in which chloroform is reacted with potassium hydroxide or sodium hydroxide and thereby converted to dichlorocarbene ($CCl_2$).

It was however found that, even when desflurane containing 250 ppm chloroform was brought into contact with a 30% aqueous solution of sodium hydroxide, the concentration of the chloroform was merely decreased to 100 ppm and was not decreased to a detection limit (1 ppm) or lower (see the after-mentioned Comparative Example 1). It was also found that, when desflurane containing 250 ppm chloroform is brought into sodium ethylate in ethanol, there occurred not only decomposition of the chloroform but also decomposition of the target desflurane (see the after-mentioned Comparative Example 5).

The chloroform is suspected to induce arrhythmia, to have a detrimental effect on the liver and kidney and to have carcinogenicity. It is thus desired that the chloroform is removed as much as possible from the desflurane. In the United States of America, the concentration of chloroform in desflurane is restricted to 60 ppm or lower (see U.S. Pharmacopoeia USP 39). In the Europe, the concentration of chloroform in desflurane is restricted to 20 ppm or lower (see European Pharmacopoeia EP 9.0).

The other trihalomethanes are also suspected to have carcinogenicity and to have a detrimental effect on the human health. It is therefore very important to remove the trihalomethanes including chloroform from the desflurane for use of the desflurane as an inhalation anesthetic.

1. Purification Method of Desflurane

A purification method of desflurane according to the present invention includes bringing a mixture containing desflurane (i.e. difluoromethyl-1,2,2,2-tetrafluoroethyl ether of the formula (1)) and a trihalomethane into contact with a base in the presence of water and a phase transfer catalyst, thereby decomposing the trihalomethane.

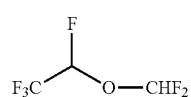
(1)

[Trihalomethane]
Examples of the trihalomethane decomposed in the purification method of the desflurane according to the present invention include chloroform, dichlorofluoromethane, chlorodifluoromethane and trifluoromethane. However, any trihalomethane other than those azeotropic with the desflurane can be removed by distillation without being brought into contact with the base. As the trihalomethane decomposed in the purification method of the desflurane according to the present invention, preferred is chloroform.

[Phase Transfer Catalyst]

There is no particular limitation on the phase transfer catalyst used in the purification method of the desflurane according to the present invention. For example, there can be used a phase transfer catalyst belonging to ammonium salts, phosphonium salts or ethers. With the use of the phase transfer catalyst, the reaction of the trihalomethane and the base proceeds smoothly.

Examples of the phase transfer catalyst include: ammonium salts such as tetrabutylammonium bromide, tetraethylammonium chloride, tributylbenzylammonium chloride and tetrabutylammonium iodide; phosphonium salts such as tetrabutylphosphonium bromide, triphenylethylphosphonium bromide and triphenylmethylphosphonium bromide; 1,4,7,10,13,16-hexaoxacyclooctadecane (commonly called 18-crown 6-ether); and polyethylene glycols (commonly called polyethylene glycol 200, polyethylene glycol 400 etc., CAS No.: 25322-68-3).

Among others, the phase transfer catalyst is preferably an ammonium salt that has high solubility in water and allows the reaction of the trihalomethane and the base to proceed smoothly. Particularly preferred is tetrabutylammonium chloride. The above phase transfer catalysts can be used solely or in combination of two or more kinds thereof. Further, the above phase transfer catalysts are available from reagent makers or chemical makers such as Wako Pure Chemical Corporation, Tokyo Chemical Industry Co., Ltd. etc.

The amount of the phase transfer catalyst used is preferably 0.001 mass % to 30 mass % based on the total mass of the desflurane. The amount of the phase transfer catalyst used is more preferably 0.01 mass % to 20 mass %, still more preferably 0.01 mass % to 10 mass %. When the amount of the phase transfer catalyst used is less than 0.001 mass %, the trihalomethane may not be removed sufficiently. There is no need to use the phase transfer catalyst in an amount exceeding 30 mass %.

[Base]

In the purification method of the desflurane according to the present invention, a hydrogencarbonate, carbonate or hydroxide of an alkali metal can be used as the base.

Examples of the base include: alkali metal hydrogencarbonates such as lithium hydrogencarbonate, sodium hydrogencarbonate and potassium hydrogencarbonate; alkali metal carbonates such as lithium carbonate, sodium carbonate and potassium carbonates; and alkali metal hydroxides such as lithium hydroxide, sodium hydroxide and potassium hydroxide.

Among others, the base is preferably an alkali metal hydroxide that has high solubility in water and allows the reaction of the trihalomethane and the base to proceed smoothly. Particularly preferred is sodium hydroxide. The above bases can be used solely or in combination of two or more kinds thereof. Further, the above bases are available from reagent makers or chemical makers such as Wako Pure Chemical Corporation, Tokyo Chemical Industry Co., Ltd. etc.

The amount of the base used is varied depending on the kind of the base, and is preferably 0.001 mass % to 100 mass %, more preferably 0.1 mass % to 50 mass %, based on the total mass of the desflurane. When the amount of the base used is less than 0.001 mass %, the trihalomethane may not be removed sufficiently. The excessive use of the base is not particularly limited. It is however preferable that the amount of the base used is small so as to facilitate separation of the desflurane and, more specifically, two-phase separation of the desflurane after the removal of the trihalomethane. There is no need to use the base in an amount exceeding 100 mass %.

During the reaction, the concentration of the base in the aqueous reaction solution is preferably 1 mass % to 50 mass %, more preferably 10 mass % to 30 mass %. When the concentration of the base in the aqueous reaction solution is lower than 1 mass %, the trihalomethane may not be removed sufficiently. The high concentration of the base in the aqueous reaction solution is not particularly limited. However, there is a possibility that the base may get deposited when the concentration of the base in the aqueous reaction solution is high. There is no need that the concentration of the base in the aqueous reaction solution exceeds 50 mass %.

[Temperature]

In the purification method of the desflurane according to the present invention, the temperature at which the mixture containing the desflurane and the trihalomethane is brought into contact with the base in the presence of the phase transfer catalyst is preferably 5° C. to 50° C. When the contact temperature is lower than 5° C., the trihalomethane may not be removed sufficiently; or the base may be solidified. When the contact temperature is high, the removal of the trihalomethane proceeds fast. There is however no need that the contact temperature exceeds 50° C.

[Pressure]

In the purification method of the desflurane according to the present invention, the pressure at which the mixture containing the desflurane and the trihalomethane is brought into contact with the base in the presence of the phase transfer catalyst is preferably 0.1 MPa to 3.0 MPa, more preferably 0.1 MPa to 1.0 MPa, still more preferably 0.1 MPa to 0.3 MPa, in terms of the absolute pressure.

[Organic Solvent]

The mixture containing the desflurane and the trihalomethane may be brought into contact with the base in the presence of only water and the phase transfer catalyst in the purification method of the desflurane according to the present invention. Alternatively, an organic solvent may be added to the reaction system. In some cases, the use of the organic solvent facilitates separation of the desflurane after the removal of the trihalomethane. As the organic solvent, preferred is an organic solvent having low water solubility.

There is no particular limitation on the kind of the organic solvent as long as the organic solvent is water-insoluble and capable of dissolving therein the desflurane and does not interfere with decomposition of the trihalomethane. There can be used an aliphatic hydrocarbon, an aromatic hydrocarbon, a nitrile, an acid amide, a lower ether etc. as the organic solvent.

Examples of the organic solvents include: aliphatic hydrocarbons such as n-pentane, n-hexane and n-heptane; aromatic hydrocarbons such as benzene, toluene and xylene; nitriles such as acetonitrile, propionitrile, phenylacetonitrile, isobutyronitrile and benzonitrile; acid amides such as dimethylformamide, dimethylacetamide, methylformamide, formamide, hexamethylphosphoric triamide and N-methylpyrrolidone; and lower ethers such as diethyl ether, tetrahydrofuran, 1,2-dimethoxyethane, 1,4-dioxane, 1,2-epoxyethane, 1,4-dioxane, dibutyl ether, t-butyl methyl ether and substituted tetrahydrofurane. These organic solvents can be used solely or in combination thereof.

A water-soluble organic solvent is not preferred because the water-soluble organic solvent remains in the aqueous phase during phase separation so that the treatment of wastewater becomes difficult.

For example, methanol or ethanol is effective for decomposition of the trihalomethane as the solubility of the desflurane and the base in methanol or ethanol is high. However, the use of methanol or ethanol lead to problems that: decomposition of the desflurane may be promoted; and phase separation cannot be performed at the recovery of the desflurane after the removal of the trihalomethane. Thus, methanol and ethanol are not preferred.

The amount of the organic solvent used is preferably 0.03 liter (hereinafter sometimes abbreviated as "L") to 10 L, more preferably 0.05 L to 10 L, still more preferably 0.07 L to 7 L, per 1 mol of the desflurane.

[Separation Step]

The purification method of the desflurane according to the present invention may include separating the desflurane and a decomposition product of the trihalomethane.

After the mixture containing the desflurane and the trihalomethane is brought into contact with the base in the presence of the phase transfer catalyst, there is obtained a reaction product in a phase-separated state. The desflurane is distributed in the organic phase, whereas the decomposition product derived from the trihalomethane is distributed in the aqueous phase. For example, sodium formate formed by contact of chloroform and sodium hydroxide is distributed in the aqueous phase. It is thus possible to recover, from the organic phase obtained by the phase separation, the desflurane without containing sodium formate.

The desflurane can preferably be obtained with high purity through e.g. distillation of the organic solvent away from the organic phase by an evaporator, flash distillation, precision distillation etc.

2. Production Method of Desflurane

A production method of desflurane according to the present invention includes bringing a mixture containing desflurane (i.e. difluoromethyl-1,2,2,2-tetrafluoroethyl ether of the formula (1)) and a trihalomethane into contact with a base in the presence of water and a phase transfer catalyst, thereby decomposing the trihalomethane, in a manner mentioned above.

In the production method of the desflurane according to the present invention, the mixture containing the desflurane and the trihalomethane may be provided as a product of the process of converting methyl-1,2,2,2-tetrafluoroethyl ether of the formula (2) to dichloromethyl-1,2,2,2-tetrafluoroethyl ether of the formula (3) by chlorination with chlorine and converting the dichloromethyl-1,2,2,2-tetrafluoroethyl ether to desflurane (i.e. difluoromethyl-1,2,2,2-tetrafluoroethyl ether of the formula (1)) by fluorination with anhydrous hydrogen fluoride.

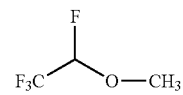

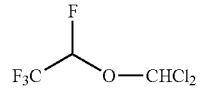

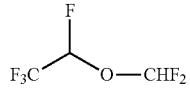

The production method of the desflurane according to the present invention may include separating the desflurane as mentioned above.

EXAMPLES

The present invention will be described in more detail below by way of the following examples. It should be understood that the present invention is not limited to the following examples.

Herein, the unit "%" of each composition analysis value means "area %" as determined from measurement of a raw material or reaction product by gas chromatography. The detector used in the gas chromatography was a hydrogen flame ionization detector (commonly called "FID"). Further, the water content was measured with the use of a Karl-Fischer measurement device.

[Formation of Desflurane]

In a pressure-resistant stainless steel reactor of 30 L internal volume equipped with a stirrer and a pressure gauge, were placed 5.00 kg of dichloromethyl-1,2,2,2-tetrafluoroethyl ether (purity 95.6%) and 5.96 kg (10 equivalents) of anhydrous hydrogen fluoride. The inside of the reactor was gradually heated to 100° C. while stirring. The reaction was performed at 100° C. for 8 hours while maintaining the pressure inside the reactor at 2.1 MPa and discharging generated hydrogen chloride out of the reaction system. The reactor was returned to room temperature and then degassed. Subsequently, 10 kg of water was added into the reactor to absorb unreacted hydrogen fluoride. The resulting reaction mixture was separated into two phases.

When the composition of the organic phase was analyzed by gas chromatography, it was found that the organic phase contained 83.8% of desflurane, 10.00% of chlorofluoromethyl-1,2,2,2-tetrafluoroethyl ether as a reaction intermediate, 0.07% of chloroform as a by-product, 0.47% of dichlorofluoromethane as a by-product and 6.70% of the other impurities in total.

The organic phase was subjected to precision distillation under atmospheric pressure by means of a distillation column having a theoretical plate number of 25. When the composition of the thus-obtained main distillation fraction was analyzed by gas chromatography, it was found that the main distillation fraction contained 99.89% of desflurane, 0.09% of chloroform and 0.02% of the other impurities in total.

[Confirmation of Azeotrope Between Desflurane and Chloroform]

The liquid-vapor equilibrium of desflurane and chloroform was measured. More specifically, 2.0 g of desflurane (boiling point: 23° C.) as simple substance was mixed with 0.14 g of chloroform (boiling point: 61.2° C.). The mixture was heated. When the concentrations of desflurane and chloroform in the resulting vapor and liquid phases were measured by gas chromatography. As a result, both of the vapor phase and the liquid phase had a composition containing 99.3% to 99.4% of desflurane and 0.06% to 0.07% of chloroform. Further, the steam temperature was 23.6° C. to 23.7° C. In this way, it was confirmed that the desflurane and the chloroform formed an azeotrope with each other.

[Purification of Desflurane]

Example 1

Into a pressure-resistant glass reactor of 100 mL internal volume equipped with a stirrer and a pressure gauge, were charged 2.00 g of desflurane containing 250 ppm of chloroform, 2.00 g of a 48 mass % aqueous solution of sodium hydroxide and 0.02 g of tetrabutylammonium bromide (hereinafter also referred to as "PTC-1") as a phase transfer catalyst.

The inside of the reactor was, while stirring, heated to 40° C. and kept heated at 40° C. for 1.5 hours. After that, the reactor was returned to room temperature and then degassed. The contents of the reactor were transferred into a separatory funnel and separated into two, organic and aqueous phases. The concentration of the chloroform in the organic phase was determined by gas chromatography to be lower than or equal to a detection limit (i.e. 1 ppm or lower). Further, the water content of the organic phase was determined by a Karl-Fischer measurement device to be 160 ppm.

The organic phase was subjected to flash distillation under atmospheric pressure, thereby yielding 1.86 g of a main distillation fraction. When the main distillation fraction was measured by gas chromatography, it was confirmed that the desflurane was obtained with a purity of 99.95% or higher and a recovery rate of 93%.

Example 2

Into a pressure-resistant glass reactor of 100 mL internal volume equipped with a stirrer and a pressure gauge, were charged 2.00 g of desflurane containing 250 ppm of chloroform, 2.00 g of a 48 mass % aqueous solution of sodium hydroxide and 0.02 g of PTC-1 as a phase transfer catalyst.

The inside of the reactor was kept stirred at room temperature (about 25° C.). After the lapse of 4 hours, the reactor was degassed. The contents of the reactor were transferred into a separatory funnel and separated into two, organic and aqueous phases. The concentration of the chloroform in the organic phase was determined by gas chromatography to be lower than or equal to a detection limit (i.e. 1 ppm or lower). Further, the water content of the organic phase was determined by a Karl-Fischer measurement device to be 150 ppm.

The organic phase was subjected to flash distillation under atmospheric pressure, thereby yielding 1.83 g of a main distillation fraction. When the main distillation fraction was measured by gas chromatography, it was confirmed that the desflurane was obtained with a purity of 99.95% or higher and a recovery rate of 92%.

Example 3

Into a pressure-resistant glass reactor of 100 mL internal volume equipped with a stirrer and a pressure gauge, were charged 2.00 g of desflurane containing 250 ppm of chloroform, 2.00 g of a 30 mass % aqueous solution of sodium hydroxide and 0.02 g of PTC-1 as a phase transfer catalyst.

The inside of the reactor was, while stirring, heated to 40° C. and kept heated at 40° C. for 7 hours. After that, the reactor was returned to room temperature and then degassed. The contents of the reactor were transferred into a separatory funnel and separated into two, organic and aqueous phases. The concentration of the chloroform in the organic phase was determined by gas chromatography to be lower than or equal to a detection limit (i.e. 1 ppm or lower). Further, the water content of the organic phase was determined by a Karl-Fischer measurement device to be 170 ppm.

The organic phase was subjected to flash distillation under atmospheric pressure, thereby yielding 1.79 g of a main distillation fraction. When the main distillation fraction was measured by gas chromatography, it was confirmed that the desflurane was obtained with a purity of 99.95% or higher and a recovery rate of 90%.

Example 4

Into a pressure-resistant glass reactor of 100 mL internal volume equipped with a stirrer and a pressure gauge, were charged 2.00 g of desflurane containing 3200 ppm of chloroform, 2.00 g of a 30 mass % aqueous solution of sodium hydroxide and 0.10 g of PTC-1 as a phase transfer catalyst.

The inside of the reactor was, while stirring, heated to 40° C. and kept heated at 40° C. for 14 hours. After that, the reactor was returned to room temperature and then degassed. The contents of the reactor were transferred into a separatory funnel and separated into two, organic and aqueous phases. The concentration of the chloroform in the organic phase was determined by gas chromatography to be lower than or equal to a detection limit (i.e. 1 ppm or lower). Further, the water content of the organic phase was determined by a Karl-Fischer measurement device to be 170 ppm.

The organic phase was subjected to flash distillation under atmospheric pressure, thereby yielding 1.83 g of a main distillation fraction. When the main distillation fraction was measured by gas chromatography, it was confirmed that the desflurane was obtained with a purity of 99.95% or higher and a recovery rate of 92%.

Example 5

Into a pressure-resistant glass reactor of 100 mL internal volume equipped with a stirrer and a pressure gauge, were charged 2.00 g of desflurane containing 250 ppm of chloroform, 2.00 g of a 48 mass % aqueous solution of potassium hydroxide and 0.02 g of PTC-1 as a phase transfer catalyst.

The inside of the reactor was, while stirring, heated to 40° C. and kept heated at 40° C. for 1.5 hours. After that, the reactor was returned to room temperature and then degassed. The contents of the reactor were transferred into a separatory funnel and separated into two, organic and aqueous phases. The concentration of the chloroform in the organic phase was determined by gas chromatography to be lower than or equal to a detection limit (i.e. 1 ppm or lower). Further, the water content of the organic phase was determined by a Karl-Fischer measurement device to be 160 ppm.

The organic phase was subjected to flash distillation under atmospheric pressure, thereby yielding 1.94 g of a main distillation fraction. When the main distillation fraction was measured by gas chromatography, it was confirmed that the desflurane was obtained with a purity of 99.95% or higher and a recovery rate of 97%.

Example 6

Into a pressure-resistant glass reactor of 100 mL internal volume equipped with a stirrer and a pressure gauge, were charged 2.00 g of desflurane containing 250 ppm of chloroform, 2.00 g of a 30 mass % aqueous solution of sodium hydroxide and 0.02 g of tetraethylammonium chloride (hereinafter also referred to as "PTC-2") as a phase transfer catalyst.

The inside of the reactor was, while stirring, heated to 40° C. and kept heated at 40° C. for 7 hours. After that, the reactor was returned to room temperature and then degassed. The contents of the reactor were transferred into a separatory funnel and separated into two, organic and aqueous phases. The concentration of the chloroform in the organic phase was determined by gas chromatography to be lower than or equal to a detection limit (i.e. 1 ppm or lower). Further, the water content of the organic phase was determined by a Karl-Fischer measurement device to be 200 ppm.

The organic phase was subjected to flash distillation under atmospheric pressure, thereby yielding 1.88 g of a main distillation fraction. When the main distillation fraction was measured by gas chromatography, it was confirmed that the desflurane was obtained with a purity of 99.95% or higher and a recovery rate of 94%.

Example 7

Into a pressure-resistant glass reactor of 100 mL internal volume equipped with a stirrer and a pressure gauge, were charged 2.00 g of desflurane containing 250 ppm of chloroform, 2.00 g of a 30 mass % aqueous solution of sodium hydroxide and 0.02 g of tributylbenzylammonium chloride (hereinafter also referred to as "PTC-3") as a phase transfer catalyst.

The inside of the reactor was, while stirring, heated to 40° C. and kept heated at 40° C. for 7 hours. After that, the reactor was returned to room temperature and then degassed. The contents of the reactor were transferred into a separatory funnel and separated into two, organic and aqueous phases. The concentration of the chloroform in the organic phase was determined by gas chromatography to be 6 ppm. Further, the water content of the organic phase was determined by a Karl-Fischer measurement device to be 180 ppm.

The organic phase was subjected to flash distillation under atmospheric pressure, thereby yielding 1.80 g of a main distillation fraction. When the main distillation fraction was measured by gas chromatography, it was confirmed that the desflurane was obtained with a purity of 99.95% or higher and a recovery rate of 90%.

Example 8

Into a pressure-resistant glass reactor of 100 mL internal volume equipped with a stirrer and a pressure gauge, were charged 2.00 g of desflurane containing 250 ppm of chloroform, 2.00 g of a 30 mass % aqueous solution of sodium hydroxide and 0.02 g of tetrabutylammonium iodide (hereinafter also referred to as "PTC-4") as a phase transfer catalyst.

The inside of the reactor was, while stirring, heated to 40° C. and kept heated at 40° C. for 7 hours. After that, the reactor was returned to room temperature and then degassed. The contents of the reactor were transferred into a separatory funnel and separated into two, organic and aqueous phases. The concentration of the chloroform in the organic phase was determined by gas chromatography to be 18 ppm. Further, the water content of the organic phase was determined by a Karl-Fischer measurement device to be 170 ppm.

The organic phase was subjected to flash distillation under atmospheric pressure, thereby yielding 1.82 g of a main distillation fraction. When the main distillation fraction was measured by gas chromatography, it was confirmed that the desflurane was obtained with a purity of 99.95% or higher and a recovery rate of 91%.

Example 9

Into a pressure-resistant glass reactor of 100 mL internal volume equipped with a stirrer and a pressure gauge, were charged 2.00 g of desflurane containing 250 ppm of chloroform, 2.00 g of a 30 mass % aqueous solution of sodium hydroxide and 0.02 g of tetrabutylphosphonium bromide (hereinafter also referred to as "PTC-5") as a phase transfer catalyst.

The inside of the reactor was, while stirring, heated to 40° C. and kept heated at 40° C. for 7 hours. After that, the reactor was returned to room temperature and then degassed. The contents of the reactor were transferred into a separatory funnel and separated into two, organic and aqueous phases. The concentration of the chloroform in the organic phase was determined by gas chromatography to be lower than or equal to a detection limit (i.e. 1 ppm or lower). Further, the water content of the organic phase was determined by a Karl-Fischer measurement device to be 140 ppm.

The organic phase was subjected to flash distillation under atmospheric pressure, thereby yielding 1.86 g of a main distillation fraction. When the main distillation fraction was measured by gas chromatography, it was confirmed that the desflurane was obtained with a purity of 99.95% or higher and a recovery rate of 93%.

Example 10

Into a pressure-resistant glass reactor of 100 mL internal volume equipped with a stirrer and a pressure gauge, were placed 2.00 g of desflurane containing 250 ppm of chloroform, 2.00 g of a 30 mass % aqueous solution of sodium hydroxide and 0.2 g of polyethylene glycol 400 (hereinafter also referred to as "PEG400") as a phase transfer catalyst.

The inside of the reactor was, while stirring, heated to 50° C. and kept heated at 50° C. for 5 hours. After that, the reactor was returned to room temperature and then degassed. The contents of the reactor were transferred into a separatory funnel and separated into two, organic and aqueous phases. The concentration of the chloroform in the organic phase was determined by gas chromatography to be lower than or equal to a detection limit (i.e. 1 ppm or lower). Further, the water content of the organic phase was determined by a Karl-Fischer measurement device to be 190 ppm.

The organic phase was subjected to flash distillation under atmospheric pressure, thereby yielding 1.80 g of a main distillation fraction. When the main distillation fraction was measured by gas chromatography, it was confirmed that the desflurane was obtained with a purity of 99.95% or higher and a recovery rate of 90%.

Example 11

Into a pressure-resistant glass reactor of 100 mL internal volume equipped with a stirrer and a pressure gauge, were charged 2.00 g of desflurane containing 250 ppm of chloroform, 2.00 g of a 30 mass % aqueous solution of sodium hydroxide and 0.20 g of polyethylene glycol 200 (hereinafter also referred to as "PEG200") as a phase transfer catalyst.

The inside of the reactor was, while stirring, heated to 40° C. and kept heated at 40° C. for 5 hours. After that, the reactor was returned to room temperature and then degassed.

The contents of the reactor were transferred into a separatory funnel and separated into two, organic and aqueous phases. The concentration of the chloroform in the organic phase was determined by gas chromatography to be lower than or equal to a detection limit (i.e. 1 ppm or lower). Further, the water content of the organic phase was determined by a Karl-Fischer measurement device to be 200 ppm.

The organic phase was subjected to flash distillation under atmospheric pressure, thereby yielding 1.79 g of a main distillation fraction. When the main distillation fraction was measured by gas chromatography, it was confirmed that the desflurane was obtained with a purity of 99.95% or higher and a recovery rate of 90%.

Example 12

Into a pressure-resistant glass reactor of 1 L internal volume equipped with a stirrer, a reflux device and a jacket, were charged 500.0 g of desflurane containing 250 ppm of chloroform, 500.0 g of a 30 mass % aqueous solution of sodium hydroxide and 5.0 g of tetrabutylammonium chloride (also referred to as "PTC-1") as a phase transfer catalyst.

Hot water of 40° C. was put inside the jacket. Then, the contents of the reactor was refluxed with stirring for 27 hours while being maintained at 40° C. The concentration of the chloroform in the resulting organic phase was determined by gas chromatography to be lower than or equal to a detection limit (i.e. 1 ppm or lower). After that, the water inside the jacket was heated to 50° C. so that the organic phase was recovered. The recovery rate of the organic phase was 94%. The water content of the organic phase was 160 ppm.

The recovered organic phase was subjected to precision distillation under atmospheric pressure by means of a distillation column having a theoretical plate number of 10. After the precision distillation, there was yielded 465.0 g of a main distillation fraction. When the main distillation fraction was measured by gas chromatography, it was confirmed that the desflurane was obtained with a purity of 99.95% or higher and a recovery rate of 93%.

Comparative Example 1

Into a pressure-resistant glass reactor of 100 mL internal volume equipped with a stirrer and a pressure gauge, were charged 2.00 g of desflurane containing 250 ppm of chloroform and 2.00 g of a 30 mass % aqueous solution of sodium hydroxide. The inside of the reactor was, while stirring, heated to 40° C. and kept heated at 40° C. for 7 hours. After that, the reactor was returned to room temperature and then degassed. The contents of the reactor were transferred into a separatory funnel and separated into two, organic and aqueous phases. The concentration of the chloroform in the organic phase was determined by gas chromatography to be 100 ppm.

Comparative Example 2

Into a pressure-resistant glass reactor of 100 mL internal volume equipped with a stirrer and a pressure gauge, were charged 2.00 g of desflurane containing 250 ppm of chloroform and 0.40 g of sodium hydroxide in pellet form.

The inside of the reactor was, while stirring, heated to 40° C. and kept heated at 40° C. for 3 hours. After that, the reactor was returned to room temperature and then degassed. The concentration of the chloroform in the contents of the reactor was determined by gas chromatography to be 250 ppm. It was found that the chloroform was not decomposed.

Comparative Example 3

Into a pressure-resistant glass reactor of 100 mL internal volume equipped with a stirrer and a pressure gauge, were charged 2.00 g of desflurane containing 250 ppm of chloroform, 2.00 g of a 30 mass % aqueous solution of sodium hydroxide and 2.0 g of hexafluoroisopropanol (HFIP).

The inside of the reactor was, while stirring, heated to 40° C. and kept heated at 40° C. for 7 hours. After that, the reactor was returned to room temperature and then degassed. The contents of the reactor were transferred into a separatory funnel and separated into two, organic and aqueous phases. The concentration of the chloroform in the contents of the reactor was determined by gas chromatography to be 250 ppm. It was found that the chloroform was not decomposed.

Comparative Example 4

Into a pressure-resistant glass reactor of 100 mL internal volume equipped with a stirrer and a pressure gauge, were charged 2.00 g of desflurane containing 250 ppm of chloroform, 2.00 g of a 30 mass % aqueous solution of sodium hydroxide and 2.0 g of isopropanol (IPA).

The inside of the reactor was, while stirring, heated to 40° C. and kept heated at 40° C. for 7 hours. After that, the reactor was returned to room temperature and then degassed. The contents of the reactor were transferred into a separatory funnel and separated into two, organic and aqueous phases. The concentration of the chloroform in the contents of the reactor was determined by gas chromatography to be 250 ppm. It was found that the chloroform was not decomposed.

Comparative Example 5

Into a pressure-resistant glass reactor of 100 mL internal volume equipped with a stirrer and a pressure gauge, were charged 2.00 g of desflurane containing 250 ppm of chloroform and 2.00 g of a 20 mass % ethanol solution of sodium ethylate (NaOEt).

The inside of the reactor was, while stirring, heated to 40° C. and kept heated at 40° C. for 7 hours. Then, the concentration of the chloroform in the contents of the reactor was determined by gas chromatography to be lower than or equal to a detection liquid (i.e. 1 ppm or lower). It was however confirmed by gas chromatography analysis that the desflurane was decomposed.

Comparative Example 6

Into a pressure-resistant glass reactor of 100 mL internal volume equipped with a stirrer and a pressure gauge, were charged 2.00 g of desflurane containing 250 ppm of chloroform, 2.00 g of a 30 mass % aqueous solution of sodium hydroxide and 2.0 g of methanol (MeOH).

The inside of the reactor was, while stirring, heated to 40° C. and kept heated at 40° C. for 7 hours. After that, the reactor was returned to room temperature and then degassed. Then, the concentration of the chloroform in the contents of the reactor was determined by gas chromatography to be lower than or equal to a detection liquid (i.e. 1 ppm or lower). It was however confirmed by gas chromatography analysis that the desflurane was decomposed.

The results of the decomposition of the chloroform in the desflurane during Examples 1 to 11 are summarized in TABLE 1.

| | Charging | | Conditions | | Purity (%) | Results Conc. (ppm) of chloroform | |
|---|---|---|---|---|---|---|---|
| | Kind of base (Conc.: %) | Kind of phase transfer catalyst (Charge amount: g) | Temp. (° C.) | Time (hr) | of desflurane after distillation | Before reaction | After reaction |
| Example 1 | NaOH (48) | PTC-1 (0.02) | 40 | 1.5 | 99.95 or higher | 250 | N.D. |
| Example 2 | NaOH (48) | PTC-1 (0.02) | 25 | 4 | 99.95 or higher | 250 | N.D. |
| Example 3 | NaOH (30) | PTC-1 (0.02) | 40 | 7 | 99.95 or higher | 250 | N.D. |
| Example 4 | NaOH (30) | PTC-1 (0.10) | 40 | 14 | 99.95 or higher | 3200 | N.D. |
| Example 5 | KOH (48) | PTC-1 (0.02) | 40 | 1.5 | 99.95 or higher | 250 | N.D. |
| Example 6 | NaOH (30) | PTC-2 (0.02) | 40 | 7 | 99.95 or higher | 250 | N.D. |
| Example 7 | NaOH (30) | PTC-3 (0.02) | 40 | 7 | 99.95 or higher | 250 | 6 |
| Example 8 | NaOH (30) | PTC-4 (0.02) | 40 | 7 | 99.95 or higher | 250 | 18 |
| Example 9 | NaOH (30) | PTC-5 (0.02) | 40 | 7 | 99.95 or higher | 250 | N.D. |
| Example 10 | NaOH (30) | PEG400 (0.20) | 50 | 5 | 99.95 or higher | 250 | N.D. |
| Example 11 | NaOH (30) | PEG200 (0.20) | 40 | 5 | 99.95 or higher | 250 | N.D. |
| Example 12 | NaOH (30) | PTC-1 (5.00) | 40 | 27 | 99.95 or higher | 250 | N.D. |

Examples 1 to 11:
Charge amount:
Deslurane 2.00 g
Aqueous base solution 2.00 g
Example 12:
Charge amount:
Desflurane 500.0 g
NaOH (30) 500.0 g
NaOH: Sodium hydroxide
KOH: Potassium hydroxide
PEG: Polyethylene glycol
N.D.: Lower than or equal to detection limit (1 ppm or lower)

The phase transfer catalysts recited in TABLE 1 are shown below.

PTC-1
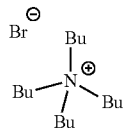

PTC-2
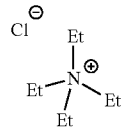

PTC-3
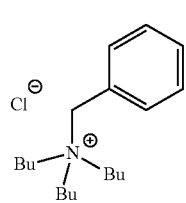

-continued

PTC-4
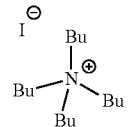

PTC-5
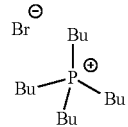

The results of the decomposition of the chloroform in the desflurane during Comparative Examples 1 to 6 are summarized in TABLE 2.

| | Charging | | Conditions | | Purity (%) | Results Conc. (ppm) of chloroform | |
|---|---|---|---|---|---|---|---|
| | Kind of base (Conc.: %) Change amount (g) | Kind of solvent Charge amount (g) | Temp. (° C.) | Time (hr) | of desflurane after operation | Before reaction | After reaction |
| Comparative Example 1 | NaOH (30) 2.00 | none | 40 | 7 | not measured | 250 | 100 |
| Comparative Example 2 | NaOH pellet 0.5 | none | 40 | 3 | not measured | 250 | 250 |

| | Charging | | Conditions | | Results | | |
|---|---|---|---|---|---|---|---|
| | Kind of base | | | | Purity (%) | Conc. (ppm) of chloroform | |
| | (Conc.: %) Change amount (g) | Kind of solvent Charge amount (g) | Temp. (° C.) | Time (hr) | of desflurane after operation | Before reaction | After reaction |
| Comparative Example 3 | NaOH (30) 2.00 | HFIP 2.00 | 40 | 7 | not measured | 250 | 250 |
| Comparative Example 4 | NaOH (30) 2.00 | IPA 2.00 | 40 | 7 | not measured | 250 | 250 |
| Comparative Example 5 | NaOEt (20) 0.40 | EtOH 1.60 | 40 | 7 | decomposed | 250 | N.D. |
| Comparative Example 6 | NaOH (30) 2.00 | MeOH 2.00 | 40 | 7 | decomposed | 250 | N.D. |

Charge Amount:
Desflurane 2.00 g
NaOH: Sodium Hydroxide
HFIP: Hexafluoroisopropanol HC(CF$_3$)$_2$OH
OPA: Isopropanol
EtOH: Ethanol
MeOH: Methanol
N.D: Lower than or equal to detection limit (1 ppm or lower)

The invention claimed is:

1. A purification method of difluoromethyl-1,2,2,2-tetrafluoroethyl ether, comprising: bringing a mixture containing difluoromethyl-1,2,2,2-tetrafluoroethyl ether of the formula (1) and a trihalomethane into contact with a base in the presence of water and a phase transfer catalyst, thereby decomposing the trihalomethane

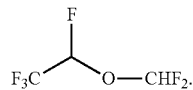
(1)

2. The purification method of difluoromethyl-1,2,2,2-tetrafluoroethyl ether according to claim 1, wherein the trihalomethane is chloroform.

3. The purification method of difluoromethyl-1,2,2,2-tetrafluoroethyl ether according to claim 1, wherein the phase transfer catalyst is an ammonium salt phase transfer catalyst.

4. The purification method of difluoromethyl-1,2,2,2-tetrafluoroethyl ether according to claim 1, wherein the phase transfer catalyst is used in an amount of 0.001 mass % to 30 mass % based on the total mass of the difluoromethyl-1,2,2,2-tetrafluoroethyl ether.

5. The purification method of difluoromethyl-1,2,2,2-tetrafluoroethyl ether according to claim 1, wherein the base is an alkali metal hydroxide.

6. The purification method of difluoromethyl-1,2,2,2-tetrafluoroethyl ether according to claim 5, wherein the alkali metal hydroxide is used in an amount of 0.001 mass % to 100 mass % based on the total mass of the difluoromethyl-1,2,2,2-tetrafluoroethyl ether.

7. The purification method of difluoromethyl-1,2,2,2-tetrafluoroethyl ether according to claim 1, wherein the mixture is brought into contact with the base in the presence of the phase transfer catalyst at a temperature of 5° C. to 50° C.

8. A production method of difluoromethyl-1,2,2,2-tetrafluoroethyl ether comprising:
forming dichloromethyl-1,2,2,2-tetrafluoroethyl ether of the formula (3) by chlorination of methyl-1,2,2,2-tetrafluoroethyl ether of the formula (2) with chlorine; and
forming difluoromethyl-1,2,2,2-tetrafluoroethyl ether of the formula (1) by fluorination of the dichloromethyl-1,2,2,2-tetrafluoroethyl ether with anhydrous hydrogen fluoride

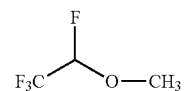
(2)

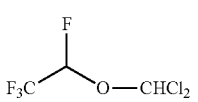
(3)

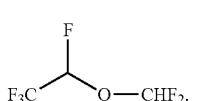
(1)

and further comprising purifying difluoromethyl-1,2,2,2-tetrafluoroethyl ether by the purification method according to claim 1.

* * * * *